US011389223B2

(12) United States Patent
Baskin

(10) Patent No.: US 11,389,223 B2
(45) Date of Patent: Jul. 19, 2022

(54) GUIDE DEVICE AND MEDICAL PROCEDURE USING THE GUIDE DEVICE

(71) Applicant: Eric S. Baskin, Brielle, NJ (US)

(72) Inventor: Eric S. Baskin, Brielle, NJ (US)

( * ) Notice: Subject to any disclaimer, the term of this patent is extended or adjusted under 35 U.S.C. 154(b) by 78 days.

(21) Appl. No.: 17/081,021

(22) Filed: Oct. 27, 2020

(65) Prior Publication Data
US 2021/0128216 A1    May 6, 2021

Related U.S. Application Data

(60) Provisional application No. 62/928,424, filed on Oct. 31, 2019.

(51) Int. Cl.
A61B 17/88    (2006.01)
A61B 17/17    (2006.01)

(52) U.S. Cl.
CPC ...... A61B 17/8897 (2013.01); A61B 17/1775 (2016.11)

(58) Field of Classification Search
CPC .................. A61B 17/8897; A61B 17/1775
See application file for complete search history.

(56) References Cited

U.S. PATENT DOCUMENTS

| H1706 H | 1/1998 | Mason |
| 5,843,085 A | 12/1998 | Graser |
| 6,391,031 B1 | 5/2002 | Toomey |
| 7,972,338 B2 | 7/2011 | O'Brien |
| 8,282,645 B2 | 10/2012 | Lawrence et al. |
| 8,377,105 B2 | 2/2013 | Buscher |
| 8,425,554 B2 | 4/2013 | Denove et al. |
| 8,617,176 B2 * | 12/2013 | Lizardi ............... A61B 17/1714 623/13.12 |
| 8,696,719 B2 | 4/2014 | Lofthouse et al. |
| 8,740,906 B2 | 6/2014 | Haines |
| 8,801,717 B2 | 8/2014 | Herdrich et al. |
| 8,870,876 B2 | 10/2014 | Lettmann et al. |
| 9,622,805 B2 | 4/2017 | Santrock et al. |
| 9,713,484 B2 * | 7/2017 | Sammarco ......... A61B 17/7241 |
| 9,750,551 B1 | 9/2017 | Nichols |
| 9,814,474 B2 | 11/2017 | Monotoya et al. |

(Continued)

FOREIGN PATENT DOCUMENTS

| WO | 98/20799 A1 | 5/1998 |
| WO | 2004/078220 A2 | 9/2004 |
| WO | 2018/202782 A2 | 11/2018 |

OTHER PUBLICATIONS

International Search Report and Written Opinion dated Jan. 8, 2021, in International Patent Application No. PCT/US2020/057541.

(Continued)

Primary Examiner — Christian A Sevilla
(74) Attorney, Agent, or Firm — Venable LLP

(57) ABSTRACT

A guide device for aiding an operator during a medical procedure (e.g., bunionectomy) includes a first frame portion, a second frame portion, and projections at end portions of the first and second frame portions. The projections are configured to receive various elongated accessories, such as a guide wire. One of the end portions includes a swivel portion that is pivotable. The guide device includes holes on at least one of the frame portions to secure the guide device to a patient and/or to attach supplemental accessories thereto.

21 Claims, 13 Drawing Sheets

(56) References Cited

U.S. PATENT DOCUMENTS

| | | | |
|---|---|---|---|
| 9,888,930 B2 | 2/2018 | Hanni et al. | |
| 9,925,010 B2* | 3/2018 | Pandya | A61B 34/20 |
| 10,159,512 B2 | 12/2018 | Robinson | |
| 10,786,292 B2 | 9/2020 | Singh et al. | |
| 2005/0143745 A1* | 6/2005 | Hodorek | A61B 17/1764 |
| | | | 606/87 |
| 2006/0264961 A1 | 11/2006 | Murray-Brown | |
| 2008/0147079 A1* | 6/2008 | Chin | A61B 17/7082 |
| | | | 606/102 |
| 2010/0152740 A1* | 6/2010 | O'Reilly | A61B 17/17 |
| | | | 606/104 |
| 2011/0153018 A1* | 6/2011 | Walters | A61B 17/1764 |
| | | | 623/13.14 |
| 2013/0018424 A1 | 1/2013 | Subik | |
| 2014/0081281 A1* | 3/2014 | Felder | A61B 17/17 |
| | | | 606/96 |
| 2016/0038186 A1 | 2/2016 | Herzog et al. | |
| 2017/0164989 A1 | 6/2017 | Weiner et al. | |
| 2018/0110530 A1 | 4/2018 | Wagner et al. | |
| 2018/0271569 A1 | 9/2018 | Verstreken et al. | |
| 2021/0113223 A1 | 4/2021 | Schaumann et al. | |

OTHER PUBLICATIONS

Hans-Joerg Tmka, et al., "Minimally invasive hallux valgus surgery: a critical review of the evidence"; Aug. 2013.

Pable Wagner, et al., "Proximal Rotational Metatarsal Osteotomy for Hallux Valgus (PROMO); Short-term Prospective Case Series With a Novel Technique and Topic Review"; 2018.

Nikolaus Wulker, et al.; "The Treatment of Hallux Valgus", 2012.

* cited by examiner

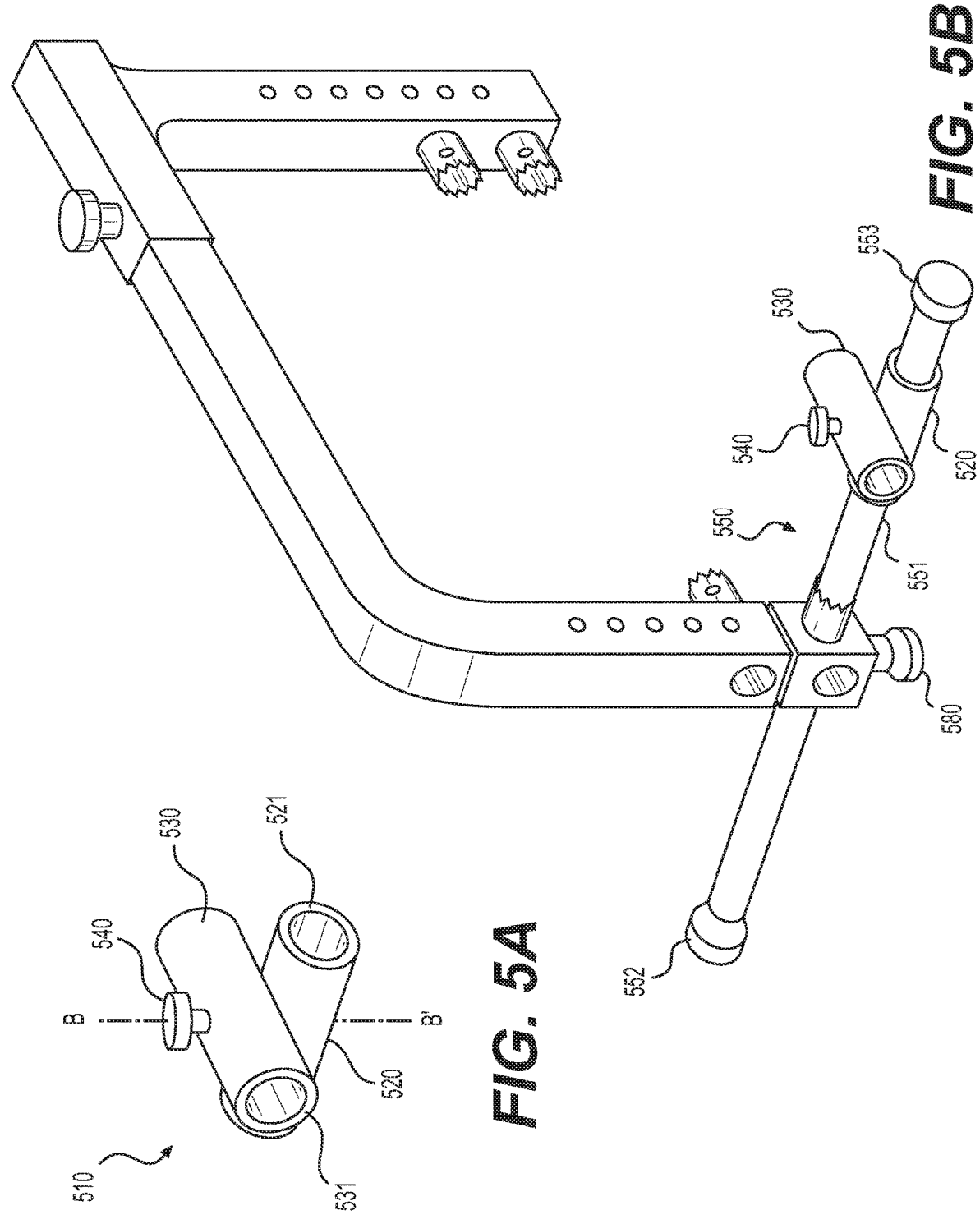

GUIDE DEVICE AND MEDICAL PROCEDURE USING THE GUIDE DEVICE

This application claims the benefit of U.S. Provisional Patent Application No. 62/928,424, filed Oct. 31, 2019, which is incorporated herein by reference in its entirety.

This invention relates to a guide device for use in medical (e.g., surgical) procedures for guiding the placement of elongated accessories such as guidewires and screws. This invention also relates to a surgical procedure performed using the guide device.

BACKGROUND OF THE INVENTION

Surgical procedures, such as bunionectomies, arthrodesis of joints, and joint replacements require a surgeon to precisely place surgical components, such as guidewires, screws, and pins, into a patient. If the surgical component is not inserted into the patient at the correct position and orientation, the component may need to be removed, and the insertion of the component may be re-attempted. Each re-insertion produces another puncture in the patient's body and increases the overall surgical procedure time, both of which increase the possibility of complications from the procedure.

A guide device may be used to assist an operator in inserting a surgical component into a patient. However, conventional guide devices are overly restrictive as to positions and orientations for which a surgical component can be inserted. For instance, some conventional guide devices may limit the insertion of a surgical component to a single position, axis plane, and/or orientation, despite such position, plane, and/or orientation not being ideal for an individual patient. As such, conventional guide devices may provide little actual assistance in targeting a desired insertion point and orientation. Moreover, conventional guide devices may require a dedicated assistant to hold the device in a desired position and orientation (or otherwise, dedicating one of the surgeon's hands to maintain such position and orientation), thereby tying up available resources during the surgical procedure.

Therefore, there is a need in the art for a device that more effectively assists a surgeon in percutaneously inserting guidewires and screws with accuracy into complex osseous anatomical structures, hidden under soft tissue and skin, reproducibly in both sagittal and traverse planes.

SUMMARY OF THE INVENTION

In one aspect, the invention provides a guide device comprising a frame, projections configured to receive elongated accessories during a medical procedure, and holes on the frame to secure the guide device to a patient.

In another aspect, the invention provides a method of performing a medical procedure, such as a bunionectomy, using a guide device according to the invention.

These and other aspects of the inventions will become apparent from the following description and the accompanying drawings.

BRIEF DESCRIPTION OF THE DRAWINGS

FIG. 5A illustrates an offset extension accessory that may be used with a guide device according to an example embodiment of the invention, and FIG. 5B illustrates a guide device with the offset extension accessory according to an example embodiment of the invention.

DETAILED DESCRIPTION OF THE PREFERRED EMBODIMENTS

Figure 1:
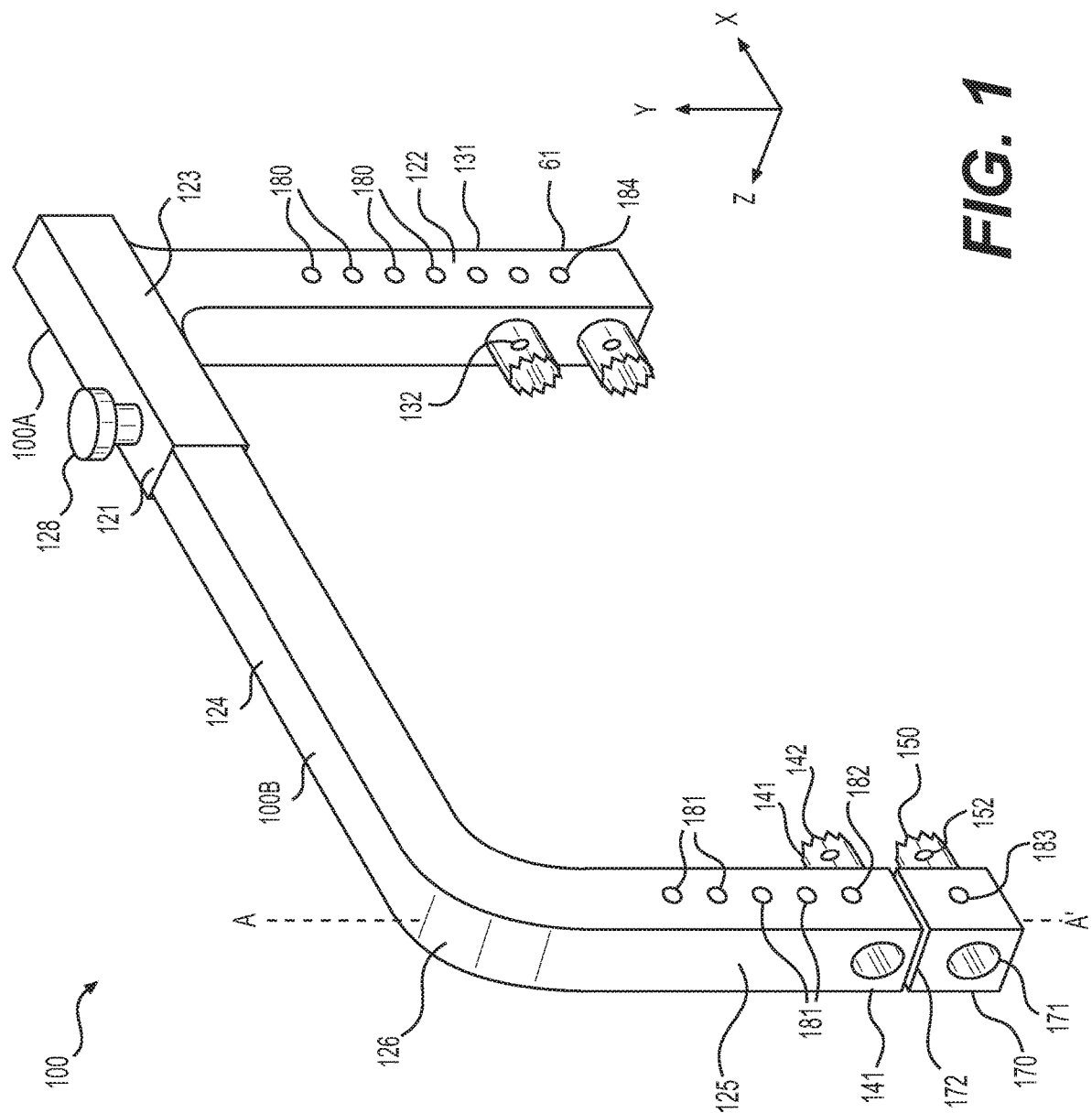
FIG. 1 illustrates a guide device according to an example embodiment of the invention.

FIG. 1 shows an example embodiment of a guide device 100 in accordance with an embodiment of the present invention. The guide device 100 includes a first frame portion 100A and a second frame portion 100B. On the first frame portion 100A, the guide device includes a first end portion 121 extending along a longitudinal direction of the guide device 100, a second end portion 122 extending along a transverse direction of the guide device 100, and a first connecting portion 123 connecting the first end portion 121 and the second end portion 122. On the second frame portion 100B, the guide device includes a third end portion 124 extending along the longitudinal direction of the guide device 100, a fourth end portion 125 extending along the transverse direction of the guide device 100, and a second connecting portion 126 connecting the third end portion 123 and the fourth end portion 125. Based on the coordinate axes illustrated in FIG. 1, the direction along the X axis will be referenced herein as the longitudinal direction of the guide device 100, the direction along the Y axis will be referenced herein as the width direction of the guide device 100, and the direction along the Z axis will be referenced herein as the vertical direction of the guide device 100.

The first end portion 121 is configured to receive the third end portion 124, so as to couple together the first frame portion 100A and the second frame portion 100B. Preferably, the first end portion 121 includes a cavity having an interior cross-sectional profile that generally corresponds with the exterior cross-sectional profile of the third end portion 124, allowing the third end portion 151 to be inserted into the cavity of the first end portion 121 without significant play. The first end portion 121 includes an adjustment mechanism 128 that controls the coupling between the first frame portion 100A and the second frame portion 100B. One example of an adjustment mechanism 128 is a thumb screw that adjusts the amount of tension between the first frame portion 100A and the second frame portion 100B. By increasing the tension, the first frame portion 100A is secured to the second frame portion 100B. This configuration permits an adjustment of distance between the second end portion 122 and the fourth end portion 124, the fastening mechanism 128 is loosened, the amount of the third end portion 124 inserted into the first end portion 121 is adjusted, and the fastening mechanism 128 is re-tightened. Of course, it will be appreciated that the fastening mechanism 128 may be implemented using other approaches other than a thumb screw that controls tension. For example, the fastening mechanism 128 may be implemented based on a ratchet mechanism with a gear rack (e.g., teeth) extending along the third end portion 124, a ratchet provided on the first end portion 121 that, when engaged with the gear rack, permits the first frame portion 100A and second frame portion 100B to be positioned closer to one another while preventing the first frame portion 100A and the second frame portion 100B from moving apart from each other, and a release mechanism that disengages the ratchet from the gear rack. Such ratchet approach is similar to the configurations used in cable zip ties and/or child safety cabinet locks.

When the first frame portion 100A and the second frame portion 100B are coupled to each other, the first end portion 121 is substantially parallel to the third end portion 124, and the second end portion 122 is substantially parallel to the fourth end portion 125. The intermediate portion 123 and the intermediate portion 126 are each curved or otherwise angled to produce such parallel orientations.

A first projection 130 is attached to the second end portion 122, and extends from the second end portion 122 towards the fourth end portion 125. The first projection 130 is preferably cylindrical or tube-like in shape, and includes a cavity extending along the longitudinal direction thereof. The cavity of the first projection 130 is configured to receive various elongated accessories, such as a guide wire (e.g., kirscher wire or "k-wire"), straight, angled, or curved soft tissue protector apparatus, threaded accessory, or a screw, that are inserted there through. The second end portion 122 includes a cavity 131 generally corresponding in position to the first projection 130 and also generally having approximately the same interior diameter as that of the cavity of the first projection 130. The cavity in the second end portion 122 allows an elongated accessory inserted through the first projection 130 to also be further inserted through the second end portion 122. Preferably, the circumferential edge of the first projection 130 includes teeth or serrations to improve gripping by the circumference edge with skin or bone, thereby preventing slippage. Optionally, the longitudinal end of the second end portion 122 is wider in the width direction of the guide device compared to the remainder of the second end portion 122 and is curved at its bottom surface (not shown), so to accommodate the external surface anatomy to securely rest on the skin of a patient. For example, the bottom surface of the second end portion 122 may have a concave curvature. An exemplary placement for such bottom surface curvature, when the device is used for a bunionectomy, is on the medial aspect of the right or left mid-foot.

A second projection 140 is attached to the fourth end portion 125, and extends from the fourth end portion 125 towards the second end portion 122. The second projection 140 is similar in structure to the first projection 130, and likewise includes a cavity configured to receive an elongated accessory inserted therethrough. The fourth end portion 125 likewise includes a cavity 141 in correspondence to the second projection 140 and having approximately the same interior diameter as that of the cavity of the second projection 140.

A swivel portion 170 is attached to the end of the fourth end portion 125 via a swivel mechanism 172. With the swivel mechanism 172, the swivel portion 170 is pivotable with respect to the fourth end portion 125 about axis A-A'. Preferably, the swivel mechanism 172 includes a retention mechanism that maintains the swivel portion 170 at an aligned angle where the swivel portion 170 and the fourth end portion 125 are aligned, yet permits an operator to adjust the swivel angle away from the aligned angle. One example of such a retention mechanism is a ball detent mechanism that provides retention at the aligned angle, yet allows for angle adjustment when a user applies sufficient rotational force exceeding the retention force. Of course, it will be appreciated that any other retention mechanism may be used without departing from the spirit of the invention.

A third projection 150 is attached to the swivel portion 170, and extends from the swivel portion 170 towards the second end portion 122. The third projection 150 is similar in structure to the first and second projections 130 and 140, and likewise includes a cavity configured to receive an elongated accessory inserted therethrough. The swivel portion 170 likewise includes a cavity 171 in correspondence to the third projection 150 and having approximately the same interior diameter as that of the cavity of the third projection 150.

A fourth projection 160 is attached to the second end portion 122, disposed further towards the end of the second end portion 122. The fourth projection 160 is similar in structure to the first, second, and third projections 130, 140, and 150, and likewise includes a cavity configured to receive an elongated accessory inserted therethrough. The second end portion 122 likewise includes a cavity 161 in correspondence to the fourth projection 160 and having approximately the same interior diameter as that of the cavity of the fourth projection 160.

The first and second projections 130 and 140 have central longitudinal lines coincident with one another, such that an elongated accessory inserted through one of the projections is received by the other projection. Similarly, the third and fourth projections 150 and 160 have central longitudinal lines coincident with one another when the swivel portion 170 is positioned at the aligned angle, such that an elongated accessory inserted through one of the projections is received by the other projection.

The first, second, third, and fourth projections 130, 140, 150, and 160 are preferably formed of a radiopaque material so that the projections are visible in a fluoroscopy image, and therefore may be used as positioning landmarks. Examples of appropriate radiopaque materials that may be used to form the components of the invention include, but are not limited to, stainless steel, various alloys, or certain plastics. On the other hand, the first frame portion 100A, second frame portion 100B, fastening mechanism 128, and the swivel portion 170 are preferably formed of a radiolucent material, such that these components are not visible on a fluoroscopy image. Examples of appropriate radiolucent materials that may be used to form the components of the invention include, but are not limited to, plastic or various alloys. The first, second, third, and fourth projections 130, 140, 150, and 160 may all be formed of the same material, or may be formed of different materials. The first frame portion 100A, second frame portion 100B, and the swivel portion 170 may all be formed of the same material, or may be formed of different materials.

In an example embodiment, the first, second, third, and fourth projections 130, 140, 150, and 160 have an exterior cross-sectional profile and an interior cross-sectional profile that are both circular, resulting in a cylindrical exterior and a cylindrical cavity. However, it will be appreciated that either one of the exterior or interior cross-sectional profiles may incorporate a different shape other than a circular shape, and/or the exterior cross-sectional profile may incorporate a different shape from the interior cross-sectional profile. For instance, in another example embodiment, the exterior cross-sectional profile is square or rectangular while the inner cross-sectional profile is circular, resulting in a box-like exterior and a cylindrical cavity.

The first, second, third, and fourth projections 130, 140, 150, and 160 will be referred to herein as inward-facing projections, inasmuch as the projections face towards the center of the guide device 100. In an example embodiment, the guide device 100 may also include outward-facing projections (not shown) opposed from and extending in the opposite direction from one or more of the first, second, third, and fourth projections 130, 140, 150, and 160. For instance, the guide device 100 may include an outward-facing projection extending from the cavity 131 in the opposite direction as that of the first projection 130 and having a central longitudinal line coincident with that of the first projection 130. Similarly, the guide device 100 may include an outward-facing projection extending from the cavity 141 in the opposite direction as that of the first projection 140 and having a central longitudinal line coincident with that of the first projection 140, an outward-facing projection extending from the cavity 151 in the opposite direction as that of the first projection 150 and having a central longitudinal line coincident with that of the first projection 150, and an outward-facing projection extending from the cavity 161 in the opposite direction as that of the first projection 160 and having a central longitudinal line coincident with that of the first projection 160. By providing these outward-facing projections, the elongated accessories inserted through the first, second, third, and fourth projections 130, 140, 150, and 160 may be even more stabilized and restricted from free play movement.

In an example embodiment, the guide device 100 also includes one or more holes 180 disposed along the second end portion 122, and one or more holes 181 disposed along the fourth end portion 125. Each hole 180 and 181 extends through the guide device 100 in the width direction of the guide device 100. The holes 180 and 181 are preferably circular and have appropriate diameters so as to receive elongated accessories (e.g., pins or wires) therethrough.

The holes 180 and 181 have at least two functions. First, the holes 180 and/or holes 181 may be used to secure the guide device 100 to a patient via an elongated accessory. For instance, an operator may secure the guide device 100 to a patient by inserting a pin through one or more of the holes 180 and/or holes 181 into the bone of a patient. By securing the guide device 100 to the patient, an operator's hands are no longer needed to hold the guide device 100, thereby freeing up the operator's hands for other involvements in the medical procedure. Second, the holes 180 and/or holes 181 may be used as mounting points to attach a supplemental device accessory, such as a supplemental projection module which will be described later. By providing multiple holes 180 and multiple holes 181, an operator may select a particular hole corresponding to a desired mounting position for the supplemental device accessory.

In an example embodiment, the guide device includes six holes 180 and three holes 181, each of which is circular. However, it will be appreciated that the holes 180 and 181 may utilize other shapes, and that different quantities and sizes of holes may be included as long as the structural rigidity of the guide device 100 remains sufficiently intact. In an example embodiment, the holes 180 (and the holes 181) are disposed at the same, regular intervals. However, it will be appreciated that the holes 180 may be disposed at a different interval from the holes 181, and/or that the holes 180 and/or holes 181 may be disposed at irregular intervals, such as at a closer interval for a certain area of the second end portion 122 or fourth end portion 125.

In an example embodiment, the guide device 100 further includes at least one additional hole 182 disposed near the end of the fourth end portion 125, at least one additional hole 183 disposed on the swivel portion 170, and at least one additional hole 184 disposed near the end of the second end portion 122. The holes 182-184 may be the same shape and size as the holes 180 and 181, or alternatively may have different shape and/or sizes. Preferably, each of the holes 182-184 has the same shape and size as the other two holes, but it will be appreciated that different shapes and/or sizes may again be incorporated. Preferably, with respect to the vertical direction of the guide device 100, the hole 182 is positioned approximately coincident with a central longitudinal line of the second projection 140, the hole 183 is positioned approximately coincident with a central longitudinal line of the third projection 150, and the hole 184 is positioned approximately coincident with a central longitudinal line of the fourth projection 160. Like the holes 180 and 181, the holes 182-184 may be used (i) for securing the guide device 100 to the patient, and/or (ii) for attaching a supplemental device accessory.

In an example embodiment, at least one of the projections includes a hole that extends through the projection in the width direction of the guide device 100. For instance, the projection 130 includes a hole 132 extending in the width direction of the guide device 100 from one radial end of the projection 130 to the other radial end, the projection 140 includes a similar hole 142, the projection 150 includes a similar hole 152, and the projection 160 includes a similar hole 162. The holes 132, 142, 152, and 162 may be the same shape and size as the holes 180 and 181 and/or the holes 182-184. Preferably, with respect to the vertical direction of the guide device 100, each of the holes 132, 142, 152, and 162 is positioned approximately coincident with a central longitudinal line of the respective projection. Like the holes 180-184, the holes 132, 142, 152, and 162 may be used (i) for securing the guide device 100 to the patient, and/or (ii) for attaching a supplemental device accessory.

Example Embodiment with Recess

Figure 2:
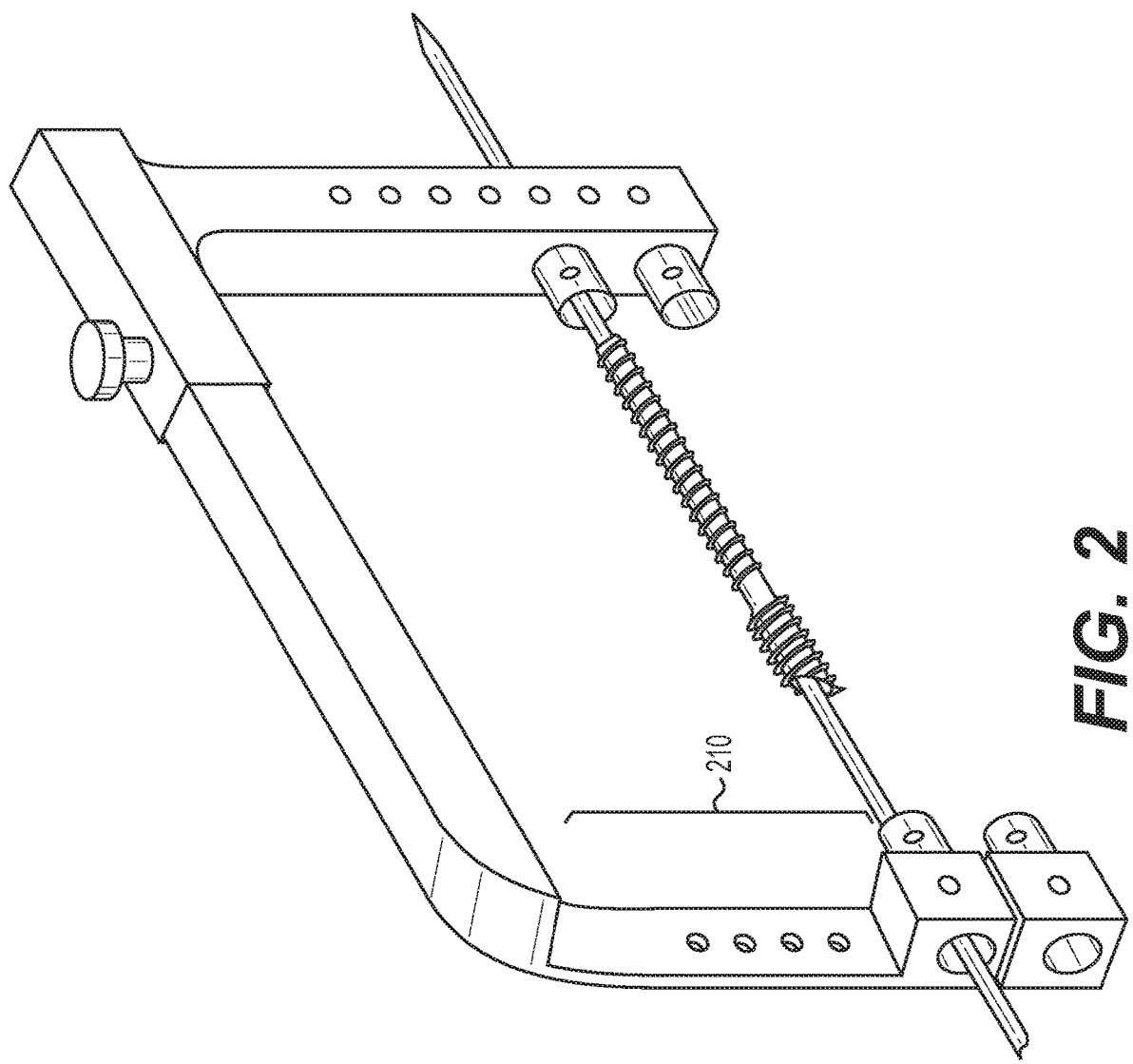
FIG. 2 illustrates a guide device according to an example embodiment of the invention.

FIG. 2 illustrates a guide device 100 in accordance with another example embodiment of the invention. The guide device 100 illustrated in FIG. 2 is similar to the one in FIG. 1, except that a recess 210 is provided in at least a portion of the fourth end portion 125 and/or the second connecting portion 124, thereby reducing the width of that portion compared with the remaining portions of the second frame portion 100B. The recess 210 allows a body part (e.g., appendage such as a toe) to be accommodated within the reduced-width area, thus preventing interference by the body appendage with positioning of the guide device 200 to a desired position and orientation.

Preferred Device Dimensions

As discussed above, each of the first, second, third, and fourth projections 130, 140, 150, and 160 is configured to receive, through its respective cavity, one or more elongated accessories. Preferably, the cavity of each of the projections is slightly larger than 4.0 mm in diameter so as to accommodate a 4.0-mm accessory (e.g., screw).

Preferably, the first end portion 121 is approximately 2.5 cm in length, the second end portion 122 is approximately 4.5 cm in length, the third end portion 124 is approximately 9.0 cm in length, and the fourth end portion 125 is approximately 4.5 cm in length. Preferably, the width of the first frame portion 100A is 0.5 cm, while the width of the second frame portion 100B is 0.2 cm. In an example embodiment where outward-facing projections are provided for cavities 141 and/or 171, preferably these projections are approximately 1.0 cm in length.

Supplemental Device Accessories

Various supplemental device accessories that may be used in conjunction with the guide device 100 will now be described.

Supplemental Projection Accessory

Figure 3B:
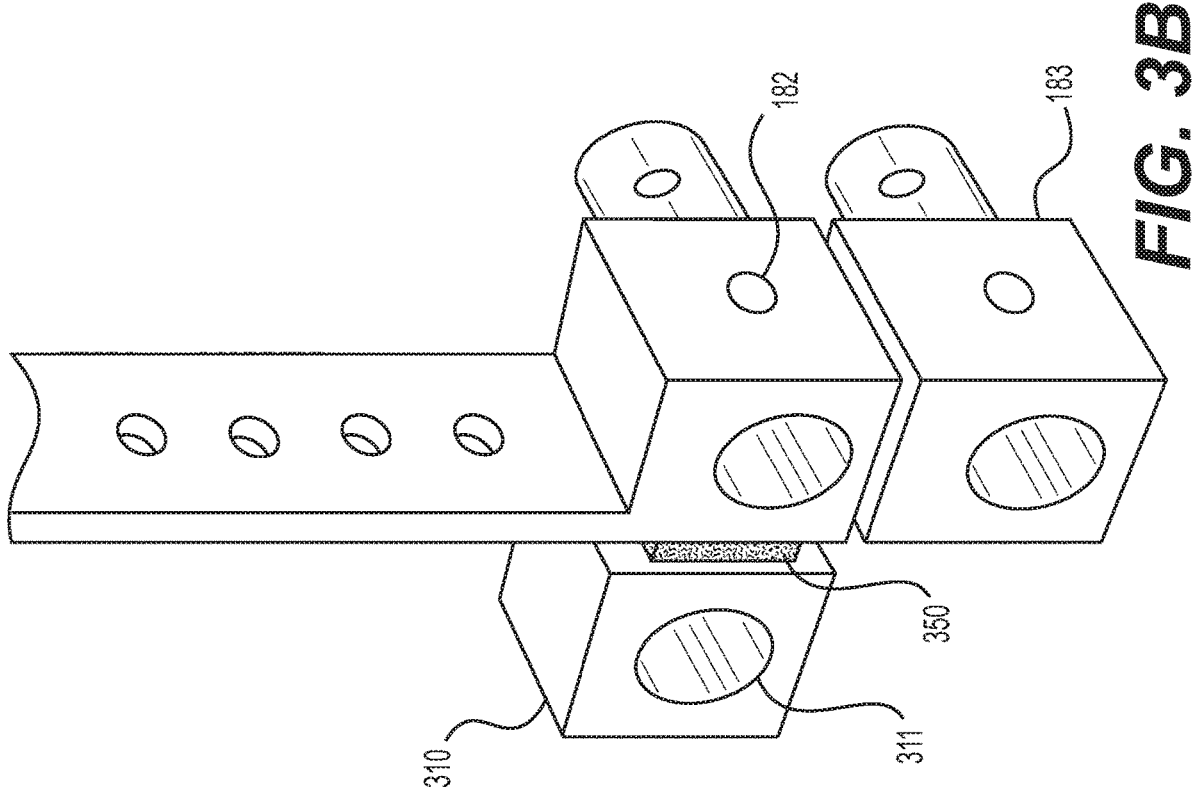
FIGS. 3A and 3B illustrate an end of a guide device according to an example embodiment of the invention.
Figure 3A:
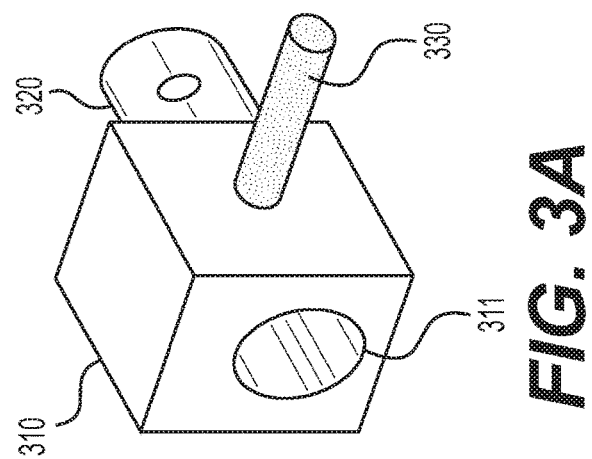

FIGS. 3A and 3B illustrate a supplemental projection module 310 that is mountable to and demountable from the guide device 100. The supplemental projection module 310 includes a projection 320 (also referred to herein as a supplemental projection) similar in structure to the first, second third, and fourth projections 130, 140, 150, and 160. The supplemental projection module 310 also includes a cavity 311, similar in structure to the cavities 141 and 171, and configured to receive an elongated accessory therethrough. The supplemental projection module 310 further includes an extension 330 for attaching the supplemental projection module 310 to the guide device 100.

By mounting the supplemental projection module 310, the guide device 100 gains an additional projection for receiving elongated accessories, notably one that is disposed offset from the existing projections 130, 140, 150, and 160 in the width direction of the guide device 100. Therefore, the supplemental projection 320 provides additional flexibility with respect to target points for inserting elongated accessories. In particular, while the projections 130, 140, 150, and 160 are all disposed along the same X-Y plane of the guide device 100, the supplemental projection 320 provides a target penetration point offset from that X-Y plane. An operator may take advantage of the offset option to ensure that the various elongated accessories (e.g., screws) inserted through the projections of the guide device into the patient are sufficiently spaced apart. Such increased spacing reduces the possibility that the inserted elongated accessories will bump or rub into each other (e.g., within the bone of the patient).

The cavity 311 of the supplemental projection module 310 may have the same diameter as that of the cavities of the first, second third, and fourth projections 130, 140, 150, and 160. Alternatively, the cavity 311 may have a different diameter from that of the cavities of the first, second third, and fourth projections 130, 140, 150, and 160. For instance, the cavities of the first, second third, and fourth projections 130, 140, 150, and 160 may have a diameter of 4.0 mm, while the cavity of the supplemental projection may have a diameter of 3.0 mm. This variance between projection cavity diameters allows for different elongated accessories to be used between the projections of different diameters.

Preferably, the supplemental projection module 310 is formed as a separate component from the guide device 100, and is mounted to the guide device 100 via inserting an extension 330 into one of the holes 182, 183, and 184. In an example embodiment, the holes 182, 183, and 184 are internally threaded, and the extension 330 is externally-threaded and threads into the holes 182, 183, and 184, thereby mounting the supplemental projection module 310 to the guide device 100. In another example embodiment, the holes 182, 183, and 184 are not threaded, and the extension 330 includes a threaded tip that, after being inserted through the holes 182, 183, and 184, receives a threaded nut on the other side of the guide device 100. However, it will be appreciated that the mounting mechanisms are not limited to these example embodiments, and any attachment structure that sufficiently secures the supplemental projection module 310 to the guide device 100 may be used.

When mounting the supplemental projection module 310 to the guide device 100, one or more spacers 350 may optionally be used. The one or more spacers 350 provides additional control as to the offset amount of the supplemental projection module 310 relative to the guide device 100. For instance, if a minimal offset amount is desired, the operator may mount the supplemental projection module 310 without using a spacer 350, such that the side face of the supplemental projection module 310 directly contacts the side of the guide device 100. If a greater offset amount is desired, the operator may insert a spacer 350 through the extension 330 between the supplemental projection module 310 and the guide device 100, thereby increasing the offset amount. For even greater offset adjustability, spacers of different thicknesses, and/or multiple adjoining spacers, may be used.

Preferably, the supplemental projection module 310, the extension 330 and the spacers 350 are formed of a radiolucent material, which may be the same material as that used to form the first and second frame portions 100A and 100B, or may be a different material. On the other hand, the supplemental projection 320 is preferably formed of a radiopaque material so that it is visible in a fluoroscopy image like the first, second, third, and fourth projections 130, 140, 150, and 160. The supplemental projection 320 may be formed of the same material used to form the first, second, third, and fourth projections 130, 140, 150, and 160, or may be formed of a different material.

Insert Accessory

Figure 4B:
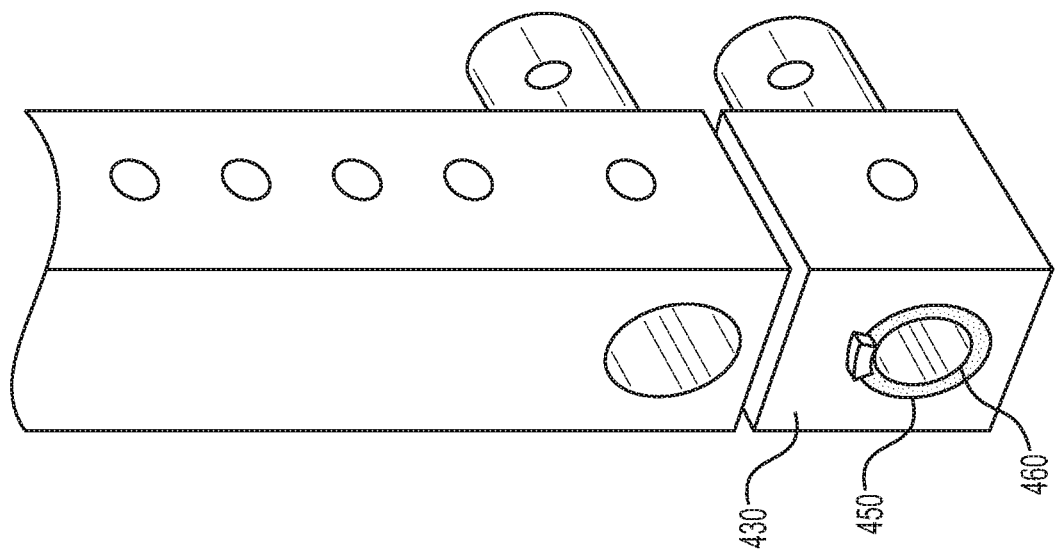
FIGS. 4A and 4B illustrate an end of a guide device according to an example embodiment of the invention.
Figure 4A:
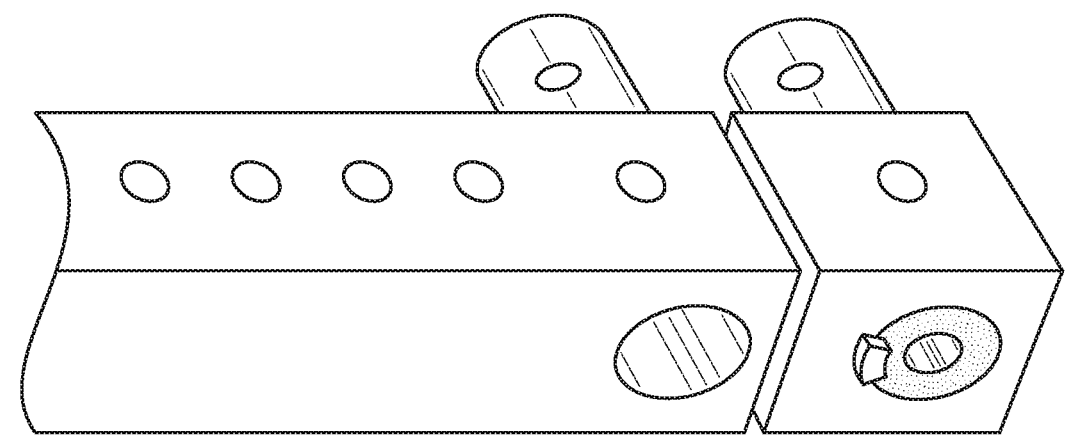

FIGS. 4A and 4B illustrate inserts that may be inserted into one or more of the cavities of the guide device 100. The inserts may be used when an elongated accessory, for insertion into a cavity and corresponding projection, has a smaller diameter than the cavity and projection. By providing the insert, the amount of play in the inserted elongated accessory is reduced, which prevents chatter and improves accuracy in targeting a desired penetration point on the body.

FIG. 4A illustrates an insert 410 that has been inserted into the cavity 171 of the swivel portion 170. While the insert 410 is depicted in the context of the cavity 171, it will be appreciated that the inserts described herein may be used with the remaining above-described cavities of the guide device 100.

The insert 410 has an exterior cross-sectional profile generally corresponding to the interior cross-sectional profile of one or more of the cavities 131, 141, 151, 161, and 311. Preferably, the exterior cross-sectional profile of the insert 410 is cylindrical and the cross-sectional profile of the respective cavity is likewise cylindrical. The insert 410 has a longitudinal length such that the insert 410, when inserted into a cavity, extends at least partially into the respective projection corresponding to the cavity. In an example embodiment, the insert 410 has a longitudinal length whereby the insert extends fully into the respective projection.

The insert 410 has a cavity 420 disposed within the interior of the profile of the insert 410, preferably disposed about a radial center of the insert 410, and extending from one longitudinal end of the insert 410 to the other longitudinal end. The cavity 420 has an appropriate diameter (also referred to herein as the "inner diameter" of the insert) for receiving elongated accessories inserted therethrough. For example, in the case that the insert 410 is designed for insertion into a 4.0 mm cavity and projection, the insert 410 may have an outer diameter of 4.0 mm and an inner diameter of 1.4 mm to receive a 1.4 mm guide wire. Alternatively, in the case that the insert 410 is designed for insertion into a 3.0 mm cavity and projection, the insert 410 may have an outer diameter of 3.0 mm and an inner diameter of 0.9 mm to receive a 0.9 mm guide wire.

Preferably, the insert 410 includes a feature for facilitating its extraction from the cavity to which it has been inserted. For instance, the insert 410 may include one or more tabs 430 extending from the cavity, which an operator may grip with a finger or a medical instrument (e.g., hemostat) to pull the insert 410 from its inserted cavity. Alternatively, the insert 410 may include an outer lip (not illustrated) having a greater diameter than that of the inserted cavity and extending from the cavity, which an operator may likewise grip with a finger or medical instrument to pull the insert 410 from its inserted cavity. Of course, it will be appreciated that any other feature for facilitating the extraction of the insert 410 may be incorporated without departing from the spirit of the invention.

Inserts of different radial thicknesses (and therefore different cavity diameters) may be used with the guide device 100. FIG. 4B illustrates an insert 450 that has a smaller radial thickness than that of the insert 410. As a result, the insert 450 has a cavity of larger diameter than that of the insert 410. The relatively larger diameter of the insert 450 allows for the insertion of larger-diameter elongated accessories through the guide device 100. Optionally, the surfaces defining the cavities 420 and 460 may be threaded (not shown) to securely accommodate threaded accessories.

Offset Extension Accessory

FIGS. 5A and 5B illustrate an offset extension accessory that may be used with the guide device 100. The offset extension accessory includes a connecting component 510 with a lower tube 520, an upper tube 530, and a pivoting mechanism 535. The lower tube 520 includes a cavity 521, and the upper tube 530 includes a cavity 531. The pivoting mechanism 535 is coupled to the lower tube 520 and the upper tube 530, and permits the upper tube 530 to be pivoted with respect to the lower tube 520 about axis B-B'.

The cavity 521 is configured to receive an extension component 550, which will be described later. The cavity 531 is configured to receive an elongated accessory therethrough. A fastening mechanism 540 is provided on the upper tube 530 to secure an elongated accessory that has been inserted therethrough, preventing movement of the elongated accessory with respect to the upper tube 530. In an example embodiment, the fastening mechanism 540 includes a thumb screw attached to the upper tube 530 that controls an amount of pressure applied to the elongated accessory inserted through the upper tube 530. That is, by turning the thumb screw in a tightening direction, an amount of pressure applied to an elongated accessory by the fastening mechanism 540 increases, thereby preventing movement of the elongated accessory. Of course, it will be appreciated that the fastening mechanism 540 may be implemented according to other implementations, such as an attachment to a jig or being used as a projection such as 130, from the distal portion of the foot to the proximal aspect (as an example), without deviating from the spirit of the invention.

The lower and upper tubes 520 and 530 are preferably formed of a radiopaque material, which may be the same material used to form the first, second, third, and fourth projections 130, 140, 150, and 160, or may be formed of a different material. The pivoting mechanism 535 and the fastening mechanism 540 may be formed of either a radiopaque or radiolucent material.

Preferably, each of the lower tube 520 and the upper tube 530 have exterior and interior cross-sectional profiles which are both circular, resulting in a cylindrical exterior and a cylindrical cavity. However, it will be appreciated that either one of the exterior or interior cross-sectional profiles may incorporate a different shape other than a circular shape, and that the exterior profile may incorporate a different shape from the interior profile. For instance, in another example embodiment, the exterior cross-sectional profile is square or rectangular while the inner cross-sectional profile is circular, resulting in a box-like exterior and a cylindrical cavity. It will further be appreciated that the exterior or interior cross-sectional profile of the lower tube 520 may differ from the corresponding profiles of the upper tube 530.

The extension component 550 is retained within both the cavity 521 and the cavity of the third projection 150. The extension component includes a central portion 551, a first end portion 552, and a second end portion 553. The central portion 551 has an exterior cross-sectional profile generally corresponding to the interior cross-sectional profile of the cavity 521. Such dimensions permit the connecting component 510 to be movable along the longitudinal direction of the extension component 550. The first end portion 552 is provided at one end of the central portion 551, and is sized with a sufficiently large cross-sectional profile that prevents the first end portion 552 from passing through the cavity of the third projection 150. Thus, the third projection 170 retains the extension component 550. The second end portion 553 is provided at the other end of the central portion 551, and is sized with a sufficiently large cross-sectional profile that prevents the second end portion 553 from passing through the cavity of the lower tube 520. In an example embodiment, the first and second end portions 552 and 553 may be identical (and thus interchangeable), if their sizes are sufficiently large to prevent their passage through the cavities of the third projection 170 and the lower tube 520. Alternatively, the first and second end portions 552 and 553 may have different dimensions.

In an example embodiment, the first and second end portions 552 and 553 are attachable and detachable from the central portion 551. In an example embodiment, the first and second end portions may include threaded extensions, while each end of the central portion 551 may include threaded cavities configured to receive the threaded extensions. In another example embodiment, either the first and second portions 552 and 553 or the central portion 551 include a biased retention mechanism (e.g., a spring) to retain the coupling between the central portion and the first and second end portions. In yet another example embodiment, one or both of the first and second end portions 552 and 553 are permanently fixed to the central portion 551 and are not detachable.

In an example embodiment, the swivel portion 170 is provided with a fastening component 580. Similar to the fastening component 540, the fastening component 580 secures an elongated accessory that has been inserted therethrough, preventing movement of the elongated accessory with respect to the third projection 150. In an example embodiment, the fastening mechanism 580 includes a thumb screw attached to the swivel portion 170 that controls an amount of pressure applied to the elongated accessory inserted through the third projection 150. That is, by turning the thumb screw in a tightening direction, an amount of pressure applied to an elongated accessory by the fastening mechanism 580 increases, thereby preventing movement of the elongated accessory. Of course, it will be appreciated that the fastening mechanism 580 may be implemented according to other implementations, without deviating from the spirit of the invention.

The offset extension accessory provides an offset retention point for elongated accessories, thereby allowing for even greater flexibility in positioning the guide device 100 at a desired orientation. For instance, where a pin has already been inserted (e.g., free-hand) into the bone of a patient and the guide device 100 is to be attached to a patient at a different orientation from that of the pin, the offset extension accessory is configured to receive such pin through the upper tube 530, while orienting the guide device 100 at a different orientation. In such an application, after an operator inserts the pin through the upper tube 530, the operator may position the guide device at a desired location with respect to the patient. With the fastening mechanisms 540 and 580 being initially disengaged, the connecting component 510 is movable along the extension component 550 and is also movable along the pin inserted through the upper tube 530. After the operator positions the guide device 100 at a desired position and orientation, the operator engages the fastening mechanisms 540 and 580 to fix the position of the guide device with respect to the patient.

Usage of the Guide Device

Figure 6A:
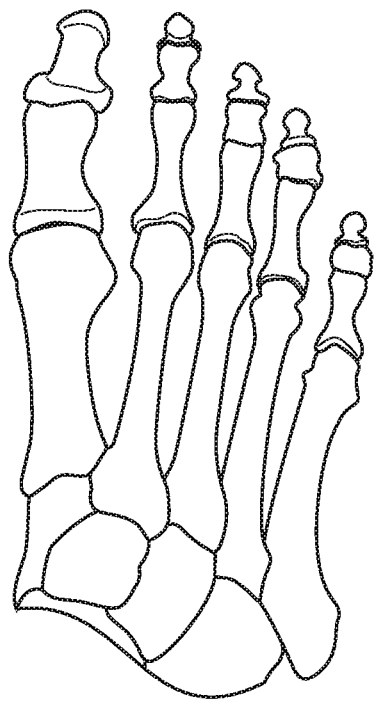
FIGS. 6A-6E illustrate a first example bunionectomy procedure that may be performed using a guide device, according to the invention.
Figure 6B:
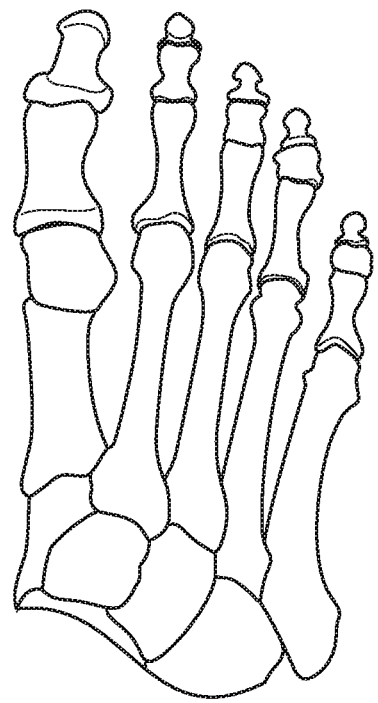
Figure 6C:
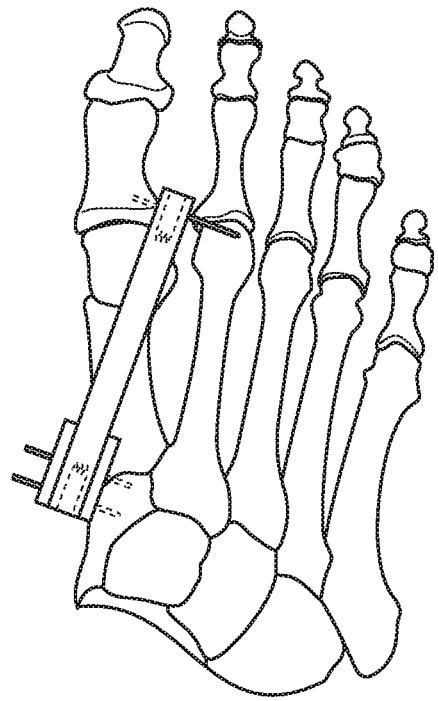
Figure 6D:
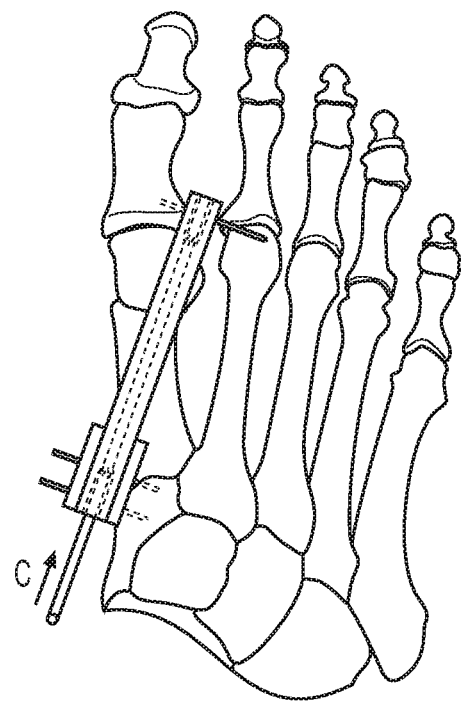
Figure 6E:
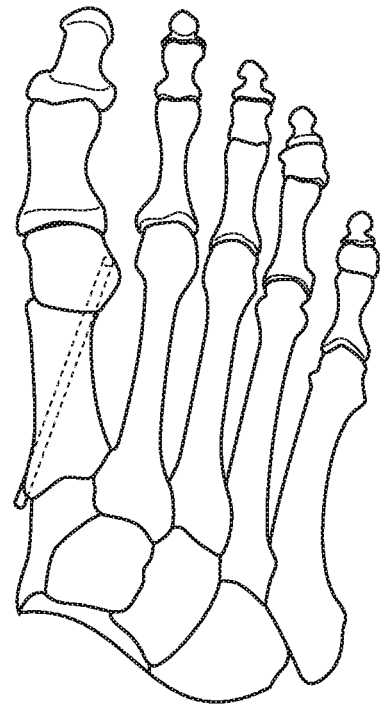

FIGS. 6A-6E illustrate one example of a bunionectomy procedure that may be used with the guide device 100. In FIG. 6A, a subject's foot prior to the procedure is shown. In FIG. 6B, a capital fragment of the subject's foot is translated into a desired corrected position. In FIG. 6C, the guide device is introduced and is pinned to the subject's foot while the surgeon or an assistant maintains the position of the translated capital fragment. The surgeon may verify the positioning of the translated capital fragment via fluoroscopy. In FIG. 6D, one or more elongated accessories (e.g., guide wire or pin) is inserted into the guide device and through the translated capital fragment in antegrade direction C, to secure the capital fragment in its corrected position. During such insertion, the surgeon or assistant must continue to hold the translated capital fragment at its corrected position. In FIG. 6E, the guide device is removed, while the one or more inserted elongated accessories remain inserted to permanently secure the translated capital fragment at its corrected position.

Figure 7A:
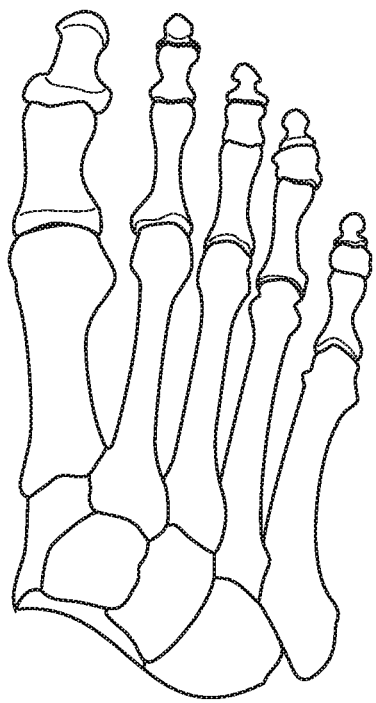
FIGS. 7A-7G illustrate a second example bunionectomy procedure that may be performed using a guide device, according to the invention.
Figure 7B:
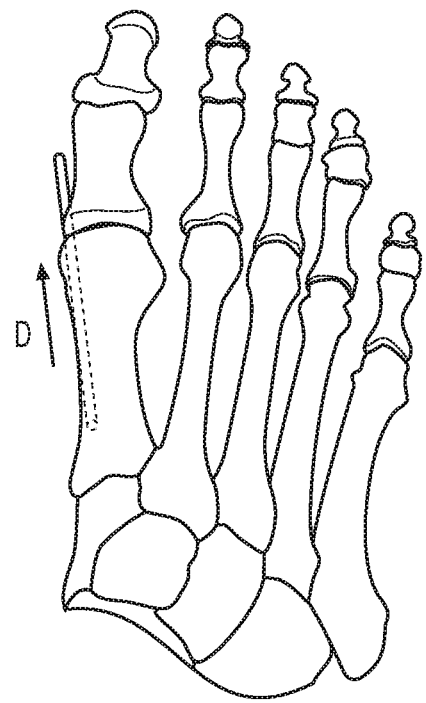
Figure 7C:
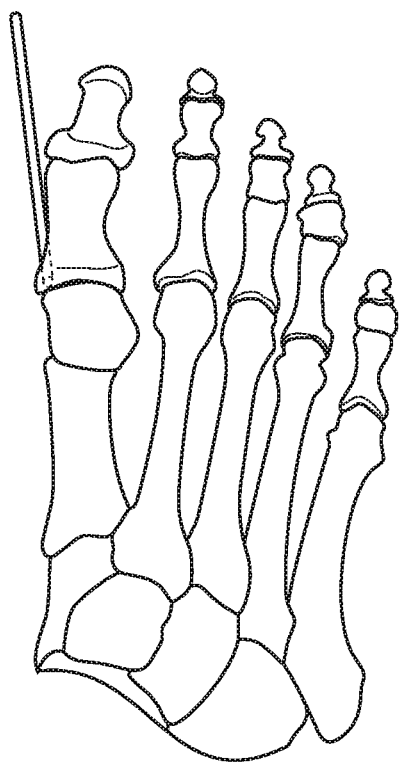
Figure 7D:
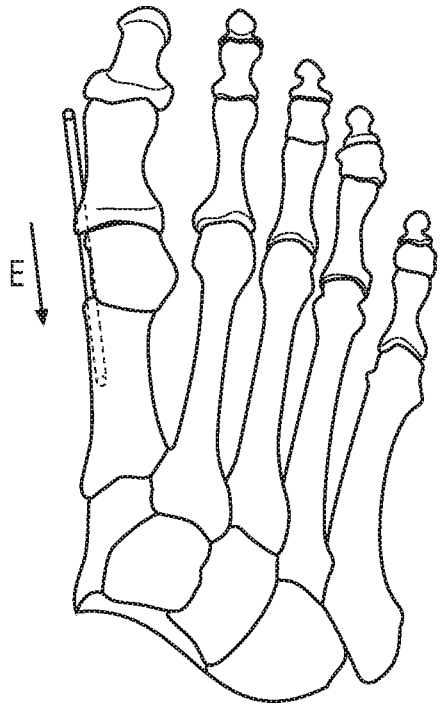
Figure 7E:
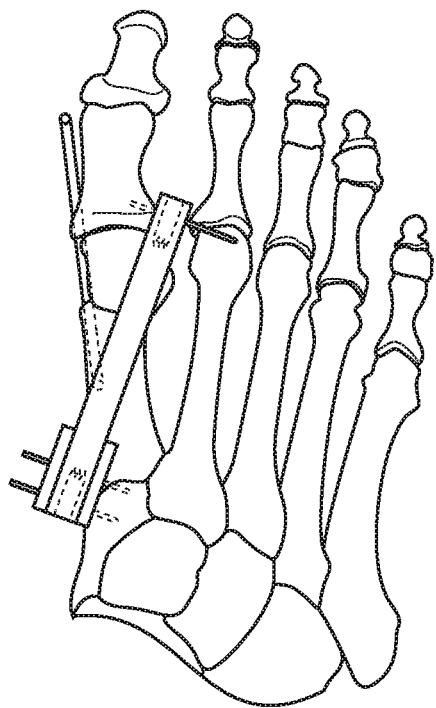
Figure 7F:
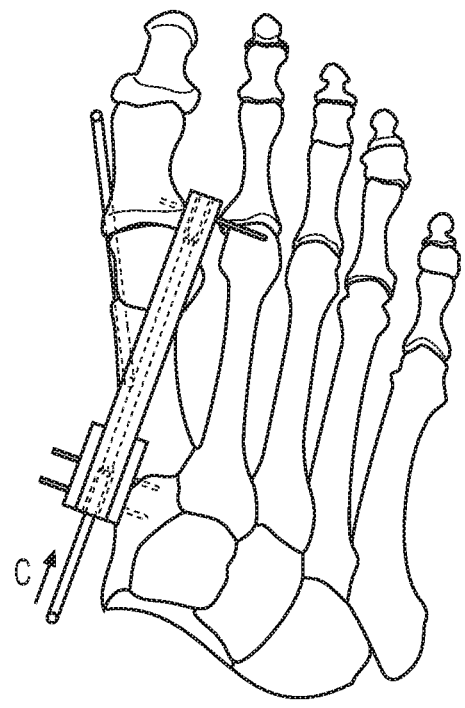
Figure 7G:
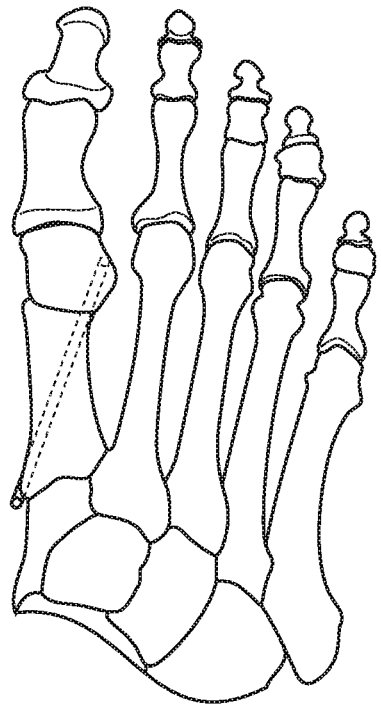

FIGS. 7A-7G illustrate another example of a bunionectomy procedure that may be used with the guide device 100. In FIG. 7A, a subject's foot prior to the procedure is shown. In FIG. 7B, a first set of one or more elongated accessories (e.g., guide wire or pin) is inserted, in antegrade direction D, through the subject's foot such that the rear end of the elongated accessory passes through the area of the subject's foot that will be translated. In FIG. 7C, a capital fragment of the subject's foot is translated into a desired corrected position. The surgeon may verify the positioning of the translated capital fragment via fluoroscopy. In FIG. 7D, the first set of one or more elongated accessories is moved in retrograde direction E, to retain the capital fragment in its corrected position. In FIG. 7E, the guide device is introduced and is pinned to the subject's foot. In FIG. 7F, a second set of one or more elongated accessories (e.g., guide wire or pin) is inserted into the guide device and through the translated capital fragment in antegrade direction C, to secure the capital fragment in its corrected position. In FIG. 7G, the guide device and the first set of one or more elongated accessories are removed, while one or more of the second set of elongated accessories remain inserted to permanently secure the translated capital fragment at its corrected position.

Figure 8A:
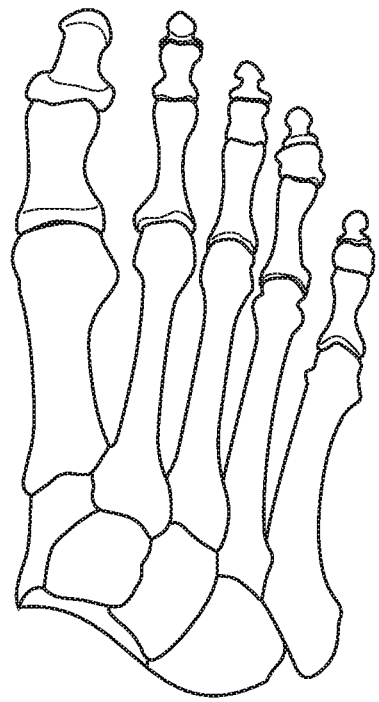
FIGS. 8A-8H illustrate a third example bunionectomy procedure that may be performed using a guide device, according to the invention.
Figure 8B:
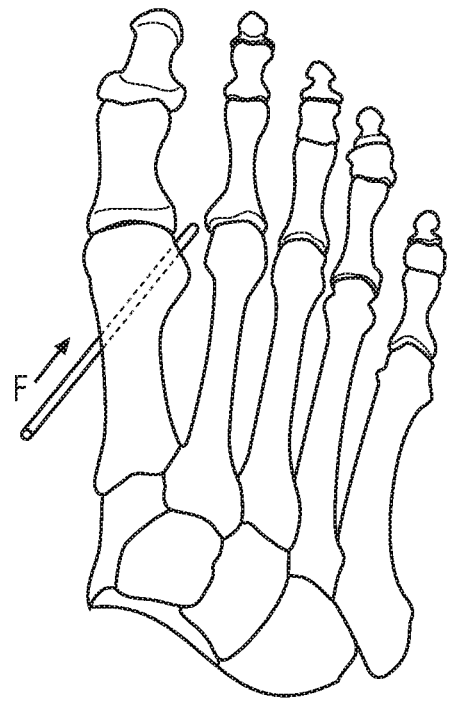
Figure 8C:
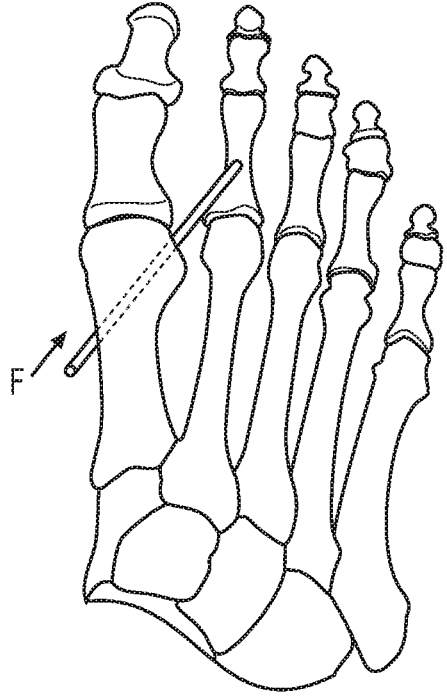
Figure 8D:
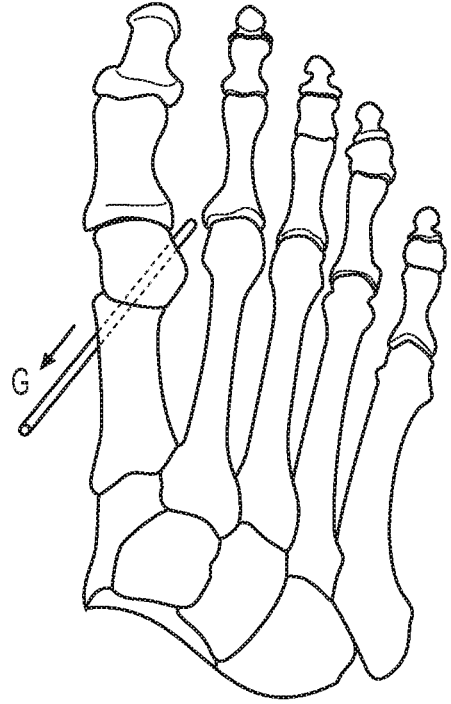
Figure 8E:
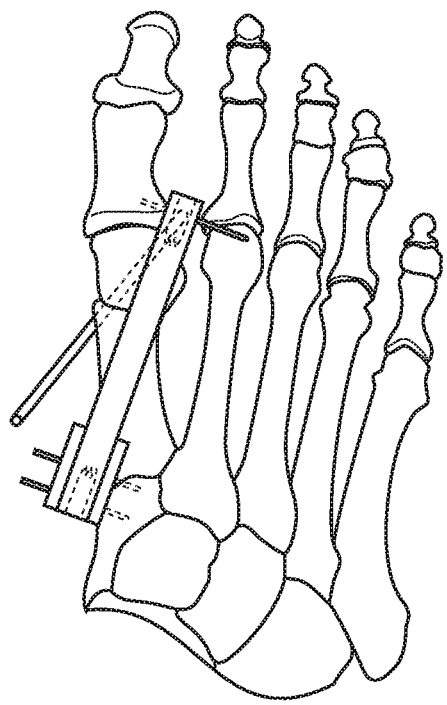
Figure 8F:
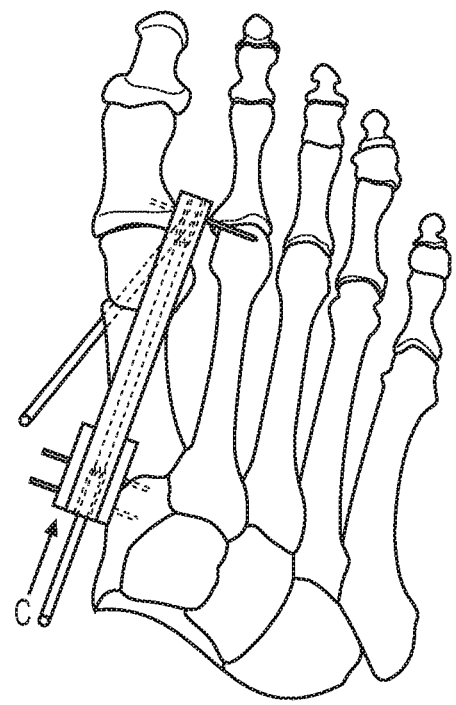
Figure 8G:
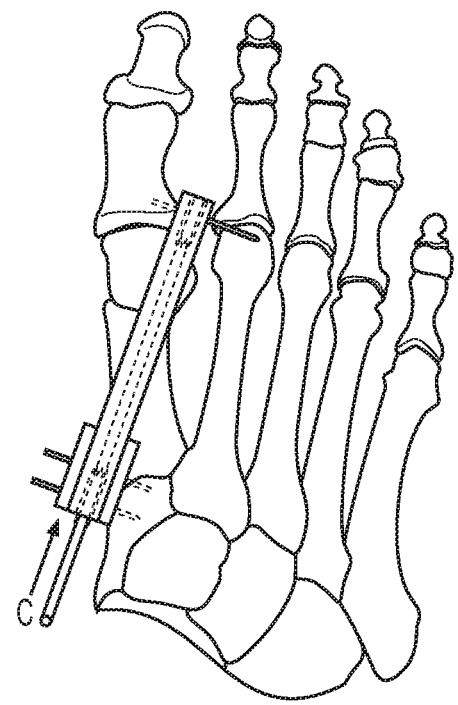
Figure 8H:
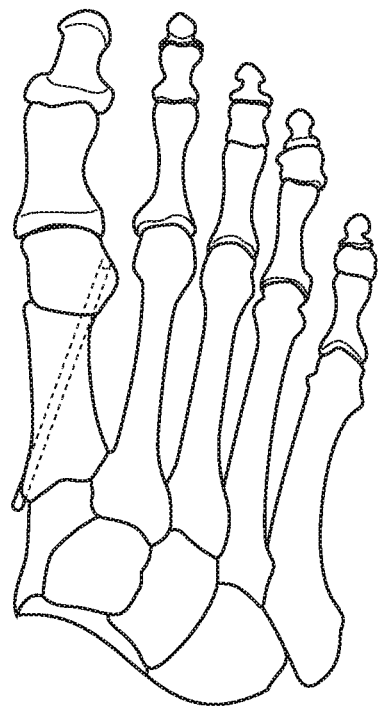

FIGS. 8A-8H illustrate another example of a bunionectomy procedure that may be used with the guide device 100. In FIG. 8A, a subject's foot prior to the procedure is shown. In FIGS. 8B and 8C, a first set of one or more elongated accessories (e.g., guide wire or pin) is inserted, in antegrade direction F, through the subject's foot such that the rear end of the elongated accessory passes through the area of the subject's foot that will be translated. In FIG. 8D, a capital fragment of the subject's foot is translated into a desired corrected position (and the surgeon may verify the positioning of the translated capital fragment via fluoroscopy), and the first set of one or more elongated accessories is moved in retrograde direction G, to retain the capital fragment in its corrected position. In FIG. 8E, the guide device is introduced, such that the first set of one or more elongated accessories is inserted through the third projection 150 and the cavity 171 of the guide device. In this regard, the swivel portion 170 of the guide device may be rotated into a desired orientation to accommodate such insertion. The guide device is then pinned to the subject's foot. In FIG. 8F, a second set of one or more elongated accessories (e.g., guide wire or pin) is inserted into the guide device and through the translated capital fragment in antegrade direction C, to secure the capital fragment in its corrected position. In FIG. 8G, the first set of one or more elongated accessories are removed. In FIG. 8H, the guide device is removed, while one or more of the second set of elongated accessories remain inserted to permanently secure the translated capital fragment at its corrected position.

Figure 9A:
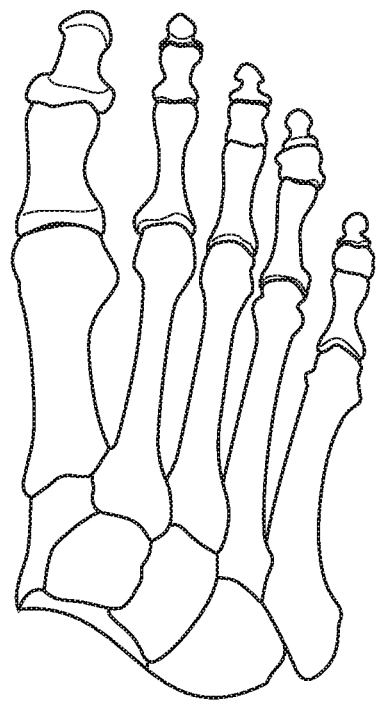
FIGS. 9A-9H illustrate a fourth example bunionectomy procedure that may be performed using a guide device and offset extension accessory, according to the invention.
Figure 9B:
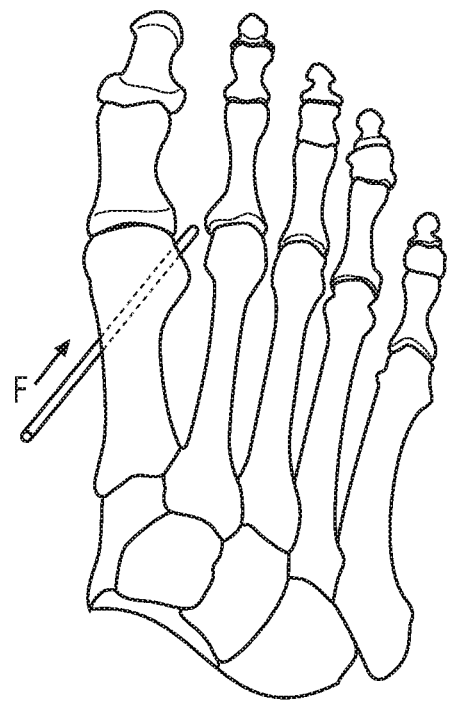
Figure 9C:
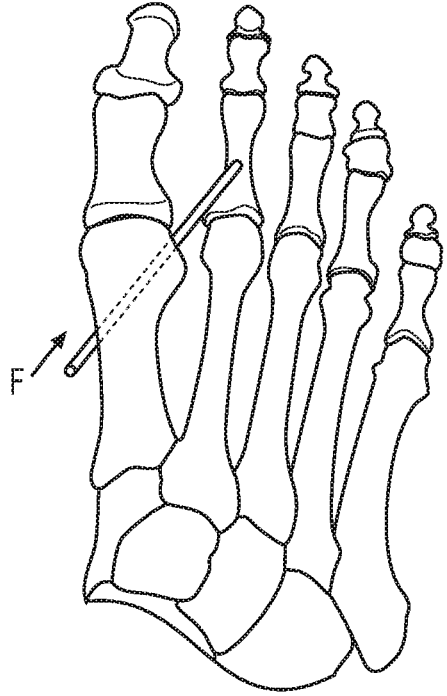
Figure 9D:
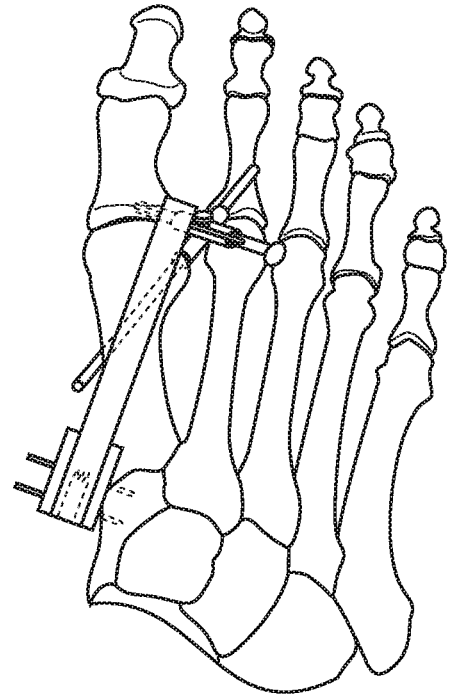
Figure 9E:
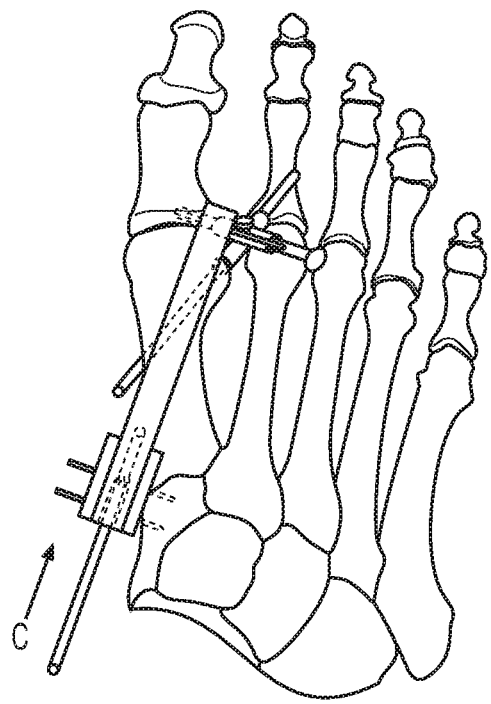
Figure 9F:
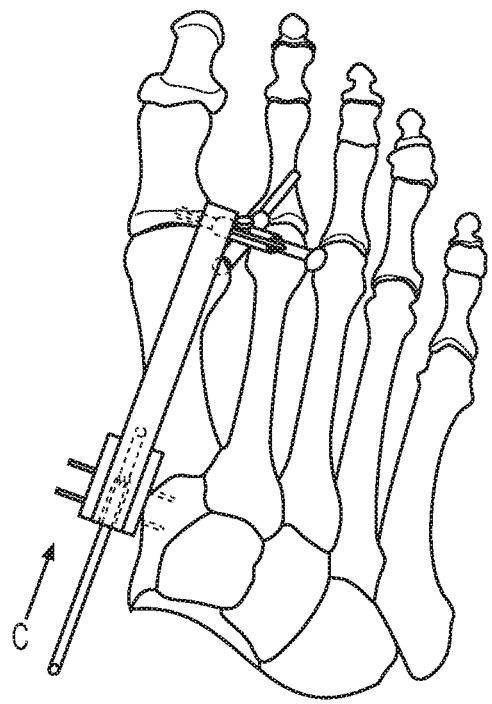
Figure 9G:
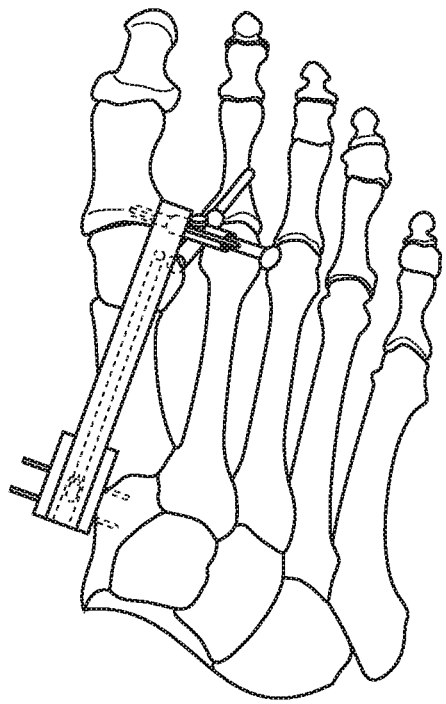
Figure 9H:
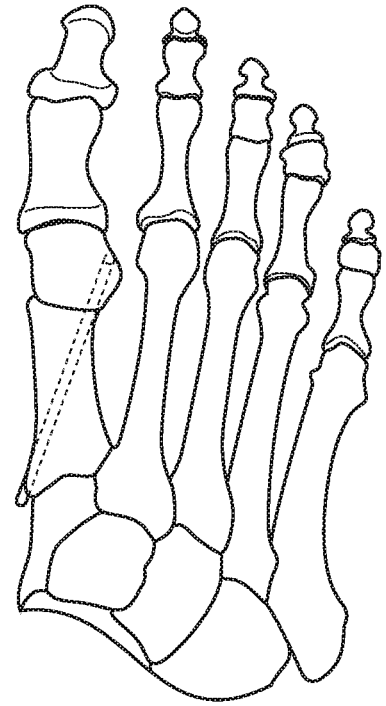

FIGS. 9A-9H illustrate another example of a bunionectomy procedure that may be used with the guide device 100 when used with the supplemental projection module 310. In FIG. 9A, a subject's foot prior to the procedure is shown. In FIGS. 9B and 9C, a first set of one or more elongated accessories (e.g., guide wire or pin) is inserted, in antegrade direction F, through the subject's foot such that the rear end of the elongated accessory passes through the area of the subject's foot that will be translated. In FIG. 9D, the guide device and supplemental projection module are introduced, such that the first set of one or more elongated accessories is inserted through the upper tube 530 of the supplemental projection module. The fastening mechanism 540 provided on the upper tube 530 is then adjusted to retain the first set of one or more elongated accessories. The guide device is then pinned to the subject's foot. In FIG. 9E, a second set of one or more elongated accessories (e.g., guide wire or pin) is partially inserted into the guide device in direction C, such that the forward end of the elongated accessories does not yet reach the area of the subject's foot that will be translated. In FIG. 9F, the first set of one or more elongated accessories is removed. In FIG. 9G, a capital fragment of the subject's foot is translated into a desired corrected position (and the surgeon may verify the positioning of the translated capital fragment via fluoroscopy), and the second set of one or more elongated accessories is further inserted in direction C, to retain the capital fragment in its corrected position. In FIG. 9H, the guide device and supplemental projection module are removed, while one or more of the second set of elongated accessories remain inserted to permanently secure the translated capital fragment at its corrected position.

It will be appreciated that the procedures described above may be used in conjunction with computer software and/or hardware that may aid the operator of the guide device. For instance, computer software and/or hardware may determine the ideal placement for the guide device on the patient's body, may provide a multi-dimensional rendering or simulation of the medical procedure involving the guide device, and/or may provide virtual reality or augmented reality features to aid an operator in handling the guide device during the medical procedure.

While preferred embodiments of the present invention have been described herein, these embodiments are provided for illustrative purposes only, and are not intended to limit the scope of the invention. Although specific configurations, structures, and processes have been shown and described, the invention is not limited to such configurations, structures, and processes. Modifications and variations are contemplated within the scope of the invention, which is to be limited only by the scope of the issued claims.

What is claimed:

1. A device comprising:
   a first frame end portion, the first frame end portion including a first cavity configured to permit passage of a medical retention device therethrough, a longitudinal direction of the first cavity being defined by a first axis; and
   a second frame end portion opposing the first frame end portion, the second frame end portion including a second cavity configured to permit passage of a medical retention device therethrough, a longitudinal direction of the second cavity being defined by a second axis,
   wherein the second frame end portion includes an adjustment mechanism, the adjustment mechanism providing user-controlled adjustment of an orientation of the second cavity between at least a first orientation and a second orientation,
   wherein when the second cavity is oriented in the first orientation, the second cavity is aligned with the first frame end portion, and
   wherein when the second cavity is oriented in the second orientation, the second cavity is not aligned with the first frame end portion.

2. The device of claim 1, wherein the first cavity extends along a width direction of the first frame end portion.

3. The device of claim 1, further comprising a second adjustment mechanism providing user-controlled adjustment of a distance between the first frame end portion and the second frame end portion.

4. The device of claim 1, wherein the second frame end portion includes a third cavity configured to permit passage of a medical retention device therethrough, a longitudinal direction of the third cavity defined by a third axis.

5. The device of claim 4, wherein the second frame end portion includes a fourth cavity configured to permit passage of a medical retention device therethrough, a longitudinal direction of the fourth cavity defined by a fourth axis.

6. The device of claim 5, wherein the fourth cavity is aligned with the first frame end portion regardless of the orientation of the second cavity.

7. The device of claim 1, wherein the first cavity extends along a width direction of the first frame end portion, and wherein the third cavity extends along a width direction of the second frame end portion.

8. The device of claim 1, further comprising a tubular projection extending from the second frame end portion and aligned with the second cavity, a longitudinal direction of the tubular projection defined by the second axis.

9. The device of claim 8, wherein when the second cavity is oriented in the first orientation, the tubular projection extends in a direction aligned with the first frame end portion, and
   wherein when the second cavity is oriented in the second orientation, the tubular projection extends in a direction offset from a direction aligned with the first frame end portion.

10. The device of claim 8, wherein the tubular projection includes a serrated edge at a longitudinal end thereof.

11. The device of claim 8, wherein the tubular projection is constructed of a radiopaque material.

12. The device of claim 1, wherein the adjustment mechanism includes a pivoting mechanism.

13. The device of claim 12, wherein the pivoting mechanism pivots about a vertical axis of the device.

14. The device of claim 13, wherein the second frame end portion includes a swivel portion, the second cavity being provided in the swivel portion, and
   wherein the pivoting mechanism provides adjustment of the orientation of the second cavity by pivot of the swivel portion.

15. The device of claim 1, further comprising a supplemental projection module, the supplemental projection module including a cavity configured to permit passage of a medical retention device therethrough,
   wherein the supplemental projection module includes a coupling mechanism configured to couple the supplemental projection module to a left side or a right side, in a width direction, of the second frame end portion.

16. The device of claim 15, wherein the second frame end portion includes a third cavity, and
   wherein the coupling mechanism of the supplemental projection module includes an extension configured to be inserted through the third cavity to couple the supplemental projection module to the side of the second frame end portion.

17. The device of claim 1, further comprising a frame intermediate portion connecting the first frame end portion and the second frame end portion.

18. The device of claim 1, wherein the second frame end portion includes a recessed portion, a width of the second frame end portion at the recessed portion being smaller than a width of the second frame end portion at portions other than the recessed portion.

19. The device of claim 1, wherein the medical retention device includes at least one of a wire, a pin, and a screw.

20. The device of claim 19, wherein a cross-sectional profile of the first cavity or a cross-sectional profile of the second cavity corresponds to a cross-sectional profile of the medical retention device.

21. A method of performing a surgical procedure comprising:
   attaching the device of claim 1 to a patient, by inserting a first medical retention device through the first cavity and into the patient;
   inserting a second medical retention device into the patient, such that the second medical retention device passes through the second cavity; and
   removing the first medical retention device from the patient.

* * * * *